(12) United States Patent
Gupta et al.

(10) Patent No.: US 6,710,185 B2
(45) Date of Patent: Mar. 23, 2004

(54) PROCESS FOR THE PREPARATION OF CELL PROLIFERATION INHIBITORS

(75) Inventors: Ashok K. Gupta, Gurnee, IL (US); Steven A. King, Gurnee, IL (US); Elaine C. Lee, Cambridge, MA (US); Howard E. Morton, Gurnee, IL (US); Daniel J. Plata, Wadsworth, IL (US); Yu-Ming Pu, Gurnee, IL (US); Padam N. Sharma, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 313 days.

(21) Appl. No.: 09/957,265

(22) Filed: Sep. 20, 2001

(65) Prior Publication Data

US 2003/0078439 A1 Apr. 24, 2003

Related U.S. Application Data

(60) Provisional application No. 60/233,963, filed on Sep. 20, 2000.

(51) Int. Cl.$^7$ ............... C07D 209/04; C07D 209/14
(52) U.S. Cl. ..................... 548/490; 548/503
(58) Field of Search ................. 548/530, 565, 548/490, 503

(56) References Cited

U.S. PATENT DOCUMENTS

| | | | |
|---|---|---|---|
| 3,102,115 A | | 8/1963 | Breuer et al. ............ 260/239 |
| 6,521,658 B1 | * | 2/2003 | Li et al. .................... 514/415 |

FOREIGN PATENT DOCUMENTS

| | | |
|---|---|---|
| WO | 00/73624 | 7/2000 |

OTHER PUBLICATIONS

Carlier et al., "Unexpected Regioselectivity in the sulfonation of leuco xanthene dyes," J. Org. Chem. 59:3232–3236 (1994).

Siddiqui et al., "Concise syntheses of the amaryllidaceae alkaloids ungerimine and hippadine via the Suzuki aryl0aryl cross coupling reaction," Tetrahedron Letters 31(11):1523–1526 (1990).

Abbott et al. "The formalin test: scoring properties fo the first and second phases of the pain response in rats", Pain 60:91–102 (1995).

Berge, J. Pharmaceutical Sciences 66:1 et seq. (1977).

Bleehen, "The effects of adenine nucleotides on cutaneous afferent nerve activity", Br. J. Pharmacol 62:573–577 (1978).

Cesare et al, Drug Dev. Res. 50:S01–02 (2000).

Cockayne et al. Drug Dev. Res. 50:005 (2000).

Cook et al., "Distinct ATP receptors on pain–sensing and stretch–sensing neurons", Nature 387:505–508 (1997).

Driessen et al., "Modulation of neural noradrealine and ATP release by angiotensin II and prostaglandin $E_2$ in guinea–pig vas deferens", Naunyn Schmiedebergs Arch Pharmacol 350:618–625 (1994).

Namasivayam et al., "Purinergic sensory neurotransmission in the urinary bladder: an invitro study in the rat", Brit J. Urol Int. 84L:854–860 (1999).

Perry et al., "2,7–disubstituted amidofluorenone derivatives as inhibitors of human telomerase," J. Med. Chem. 42:2679–2684 (1999).

Prescott et al., Methods in Cell Biology, Academic Press, New York 14:33 et seq. (1976).

Witek et al., "New pesticides and intermediates, Part VII. Some Azaalkenyl derivatives of N–phenylurea and N–phenylcarbamic acid," Polish Journal of Chemistry 55:25892600 (1981).

* cited by examiner

Primary Examiner—Peter O'Sullivan
(74) Attorney, Agent, or Firm—Gregory W. Steele; B. Gregory Donner

(57) ABSTRACT

The instant invention discloses a process for the synthesis of substituted indole cell proliferation inhibitors.

11 Claims, No Drawings

PROCESS FOR THE PREPARATION OF CELL PROLIFERATION INHIBITORS

This application claims priority to U.S. provisional application Serial No. 60/233,963, filed Sep. 20, 2000.

TECHNICAL FIELD

The instant invention is directed to a process for the preparation of cell proliferation inhibitors and to intermediates useful in the process.

BACKGROUND OF THE INVENTION

Microtubules play a key role in the regulation of cell architecture, metabolism, and division. The microtubule system of eucaryotic cells comprises a dynamic assembly and disassembly matrix in which heterodimers of tubulin polymerize to form microtubules in both normal and neoplastic cells. Within neoplastic cells, tubulin is polymerized into microtubules which form the mitotic spindle. The microtubules are then depolymerized when the mitotic spindle's use has been fulfilled. Agents which disrupt the polymerization or depolymerization of microtubules in neoplastic cells, thereby inhibiting the proliferation of these cells, comprise some of the most effective cancer chemotherapeutic agents in use.

While commonly owned U.S. Patent Provisional Application Ser. No. 60/136,542 teaches the preparation of substituted indole cell proliferation inhibitors, the synthesis is not amenable to large-scale preparation. For example, the sulfonylation of N-formylindoline is accomplished using five equivalents of chlorosulfonic acid. Upon workup, the excess chlorosulfonic acid is quenched, causing a vigorous reaction. When conducted on large amounts of material, this procedure becomes hazardous, rendering these conditions impractical for large-scale synthesis. In addition, the oxidation of the indolinesulfonamide to the corresponding indolesulfonamide is accomplished with salcomine in the presence of oxygen. The yield on this reaction is extremely low and the results are often not reproducable, making the procedure inefficient and thus impractical for large-scale synthesis.

As shown by the above examples, there is still a need in the pharmaceutical manufacturing industry for the efficient preparation of substituted indole cell proliferation inhibitors. The instant invention discloses a synthesis of cell proliferation inhibitors which offers higher overall yields and less hazardous conditions, making it amenable to large-scale preparation.

SUMMARY OF THE INVENTION

In one embodiment of the instant invention, therefore, is disclosed a process for preparing a compound of formula (5)

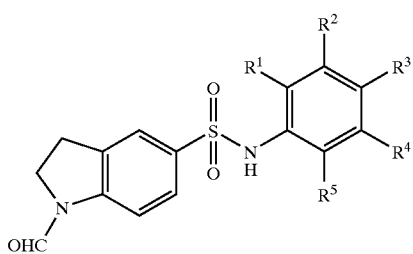

(5), or a therapeutically acceptable salt thereof, wherein
$R^1$ and $R^5$ are independently selected from the group consisting of hydrogen, alkyl, and alkoxy; and
$R^2$, $R^3$, and $R^4$ are independently selected from the group consisting of alkyl and alkoxy;
the process comprising:
(a) reacting N-formylindoline with chlorosulfonic acid and thionyl chloride; and
(b) reacting the product from step (a) with a base and a compound of formula (4) (4).

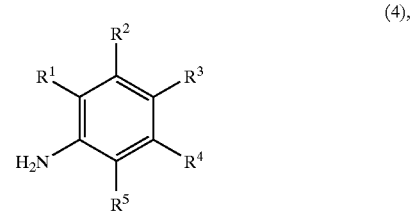

(4),

In a preferred embodiment of the instant invention is disclosed a process for preparing a compound of formula (5), or a therapeutically acceptable salt thereof, the process comprising:
(a) reacting N-formylindoline with chlorosulfonic acid and thionyl chloride at about 65° C. to about 85° C. for about 1 to about 5 hours; and
(b) reacting the product from step (a) with a carbonate salt and a compound of formula (4).

In a more preferred embodiment the compound of formula (5) is 1-formyl-N-(3,4,5-trimethoxyphenyl)-5-indolinesulfonamide.

In another embodiment of the instant invention is disclosed a process for reacting indoline with an N-formylating reagent to provide the N-formylindoline.

In another embodiment of the instant invention is disclosed a process for preparing a compound of formula (7)

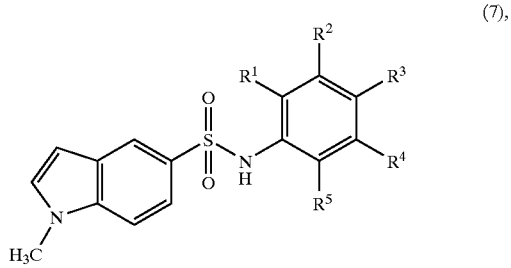

(7), the process comprising:
(a) reacting the compound of formula (5) with a reducing agent; and
(b) reacting the product of step (a) with an oxidizing agent.

In a preferred embodiment of the instant invention is disclosed a process for preparing a compound of formula (7),
the process comprising:
(a) reacting a compound of formula (5) with a reducing agent at about −5° C. to about 30° C. for about 1 to about 5 hours; and
(b) reacting the product of step (a) with an oxidizing agent at about −5° C. to about 35° C. for about 2 to about 14 hours.

In a more preferred embodiment the compound of formula (7) is 1-methyl-N-(3,4,5-trimethoxyphenyl)-1H-indole-5-sulfonamide.

In yet a further embodiment of the instant invention is disclosed a process for preparing a compound of formula (7), the process comprising:

(a) reacting the compound of formula (5) with a deformylating agent;
(b) reacting the product from step (a) with an oxidizing agent; and
(c) reacting the product from step (b) with a base and a methylating agent.

In yet an additional embodiment of the instant invention is disclosed a process for preparing a compound of formula (7a)

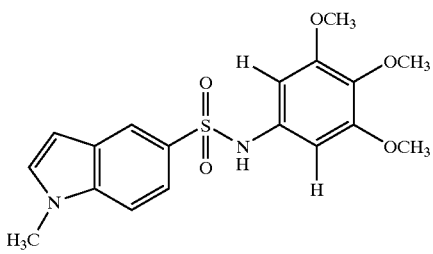

(7a), the process comprising:
(a) reacting indoline with a formylating agent;
(b) reacting the product of step (a) with chlorosulfonic acid and thionyl chloride;
(c) reacting the product of step (b) with a base and a compound of formula (4);
(d) reacting the product of step (c) with a reducing agent; and
(e) reacting the product of step (d) with an oxidizing agent.

In another embodiment of this aspect of the instant invention disclosed is a process for preparing a compound of formula (7a),
the process comprising:
(a) reacting indoline with a formylating agent;
(b) reacting the product of step (a) with chlorosulfonic acid and thionyl chloride;
(c) reacting the product of step (b) with a base and a compound of formula (4);
(d) reacting the product of step (c) with a deformylating agent;
(e) reacting the product of step (d) with an oxidizing agent; and
(f) reacting the product of step (e) with a base and a methylating agent.

In a further embodiment of the instant invention is disclosed a process for preparing a compound of formula (10a)

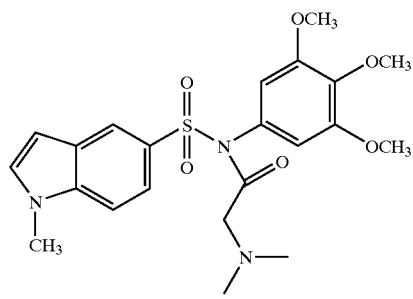

(10a), the process comprising:
reacting a compound of formula (7a) with N,N-dimethylaminoacetyl chloride hydrochloride in the presence of N,N-dimethylaminopyridine and diisopropylethylamine.

In another embodiment of the instant is disclosed a compound of formula (I)

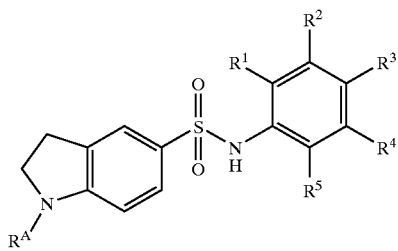

(I), or a therapeutically acceptable salt thereof, wherein
$R^1$, $R^2$, $R^3$, $R^4$, and $R^5$ are previously defined; and
$R^A$ is selected from the group consisting of hydrogen, formyl, and methyl.

DETAILED DESCRIPTION OF THE INVENTION

The instant invention is directed to processes for the preparation of cell proliferation inhibitors and to intermediates which are useful in these processes of preparation. As used in the instant specification the following terms have the meanings specified.

The term "alkoxy," as used herein, represents an alkyl group attached to the parent molecular moiety through an oxygen atom.

The term "alkyl," as used herein, represents a monovalent group of one to six carbon atoms derived from a straight or branched chain saturated hydrocarbon.

The term "base," as used herein, represents a reagent capable of accepting protons during the course of a reaction. Examples of bases include carbonate salts such as potassium carbonate, potassium bicarbonate, sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; disilylamides such as lithium hexamethyldisilazide, potassium hexamethyldisilazide, and sodium hexamethyldisilazide; trialkylamines such as triethylamine, diisopropylamine, and diisopropylethylamine; heterocyclic amines such as imidazole, pyridine, pyridazine, pyrimidine, and pyrazine; bicyclic amines such as DBN and DBU; and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "deformylating agent," as used herein, represents a reagent capable of removing a formyl group from the nitrogen atom of a molecule during the course of a reaction. Examples of deformylating agents include a mixture of hydrogen fluoride, anisole, and 1,2-ethanedithiol; a mixture of hydrochloric acid and dioxane; a mixture of hydrochloric acid and methanol; hydrazine; hydrogen peroxide; and sodium hydroxide.

The term "formylating agent," as used herein, represents a reagent capable of donating a formyl group to the nitrogen atom of a molecule during the course of a reaction. Examples of formylating agents include formic acid; 2,2,2-triethylformate; a mixture of formic acid and acetic anhydride; acetic formic anhydride; 2,3,4,5,6-pentafluorophenyl formate; ethyl formate; and a mixture of DMF and silica gel.

The term "formyl," as used herein, represents —CHO.

The term "methylating agent," as used herein, represents a reagent capable of donating a methyl group during the course of a reaction. Preferred methylating agents for the practice of the instant invention include methyl triflate, dimethyl sulfate, methyl iodide, trimethyloxonium tetrafluoroborate, and diazomethane.

The term "oxidizing agent," as used herein, represents a reagent capable of converting an indoline to an indole. Preferred oxidizing agents for the practice of the instant invention include palladium on carbon, platinum on carbon, palladium hydroxide on carbon, salcomine with oxygen, barium manganate, and 2,3-dichloro-5,6-dicyano-1,4-benzoquinone.

The term "reducing agent," as used herein, represents a reagent capable of converting a formyl group to a methyl group. Preferred reducing agents for the practice of the instant invention include sodium borohydride; a mixture of lithium aluminum hydride and aluminum trichloride; triethylsilane; borane-methyl sulfide complex; a mixture of sodium cyanoborohydride and zinc iodide; and a mixture of zinc and hydrochloric acid.

The instant compounds can exist as therapeutically acceptable salts. The term "therapeutically acceptable salt," as used herein, represents salts or zwitterions of the compounds which are water or oil-soluble or dispersible; suitable for treatment of diseases without undue toxicity, irritation, and allergic response; commensurate with a reasonable benefit/risk ratio; and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the instant compounds by reacting the sulfonamide group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the instant invention.

All of the processes of the instant invention can be conducted as continuous processes. The term "continuous process," as used herein, represents steps conducted without isolation of the intermediates.

Synthetic Processes

Abbreviations used in the descriptions of the schemes and the examples are: THF for tetrahydrofuran, DMAP for N,N-dimethylaminopyridine; DCC for dicyclohexylcarbodiimide; EDCI for 1-(3-dimethylaminopropyl)-3-ethylcarbodiimide hydrochloride; HOBT for 1-hydroxybenzotriazole hydrate; and CDI for 1,1'-carbonyldiimidazole.

The methods of this invention will be better understood in connection with the following synthetic schemes which illustrate an embodiment of this invention. It will be readily apparent to one of ordinary skill in the art that the compounds of this invention can be prepared by substitution of the appropriate reactants and agents in the synthesis shown below. It will also be apparent to one skilled in the art that the order of the steps themselves can be varied.

Scheme 1

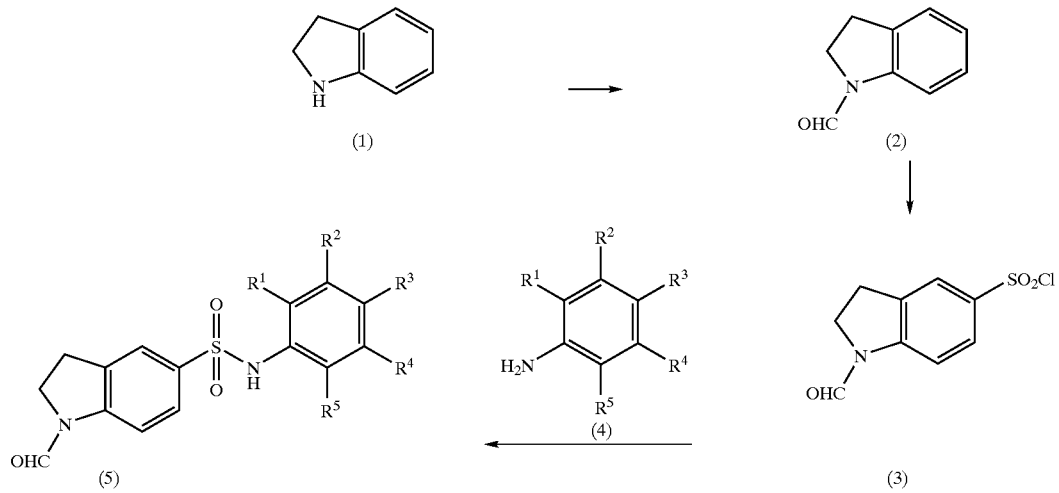

As shown in Scheme 1, indoline (1) can be converted to N-formylindoline (2) by treatment with a formylating agent. Representative formylating agents include formic acid, 2,2,2-trifluoroethylformate, acetic formic anhydride, and a mixture of formic acid and acetic anhydride. Examples of solvents used in these reactions include 1,2-dichloroethane, carbon tetrachloride, chloroform, dichloromethane, 1,2-dimethoxyethane, diethyl ether, THF, water, and mixtures thereof The reaction is conducted at about 25° C. to about 65° C. and depends on the method chosen. Reaction times are typically about 1 to about 4 hours.

N-Formylindoline (2) can be converted to 1-formyl-5-indolinesulfonyl chloride (3) by treatment with chlorosulfonic acid and thionyl chloride. Examples of solvents used in these reactions include dichloromethane, 1,2-dichloroethane, chloroform, carbon tetrachloride, and 1,2-dimethoxyethane. The reaction is conducted at about 0° C. to about 85° C. Reaction times are typically about 2 to about 6 hours.

1-Formyl-5-indolinesulfonyl chloride (3) can be converted to compounds of formula (5) by treatment with compounds of formula (4) and a base. Representative bases include sodium bicarbonate, sodium carbonate, potassium carbonate, potassium bicarbonate, and cesium carbonate. Examples of solvents used in these reactions include ethyl acetate, isopropyl acetate, THF, diethyl ether, carbon tetrachloride, and chloroform. The reaction is conducted at about 20° C. to about 50° C. and depends on the conditions chosen. Reaction times are typically about 6 to about 24 hours.

Scheme 2

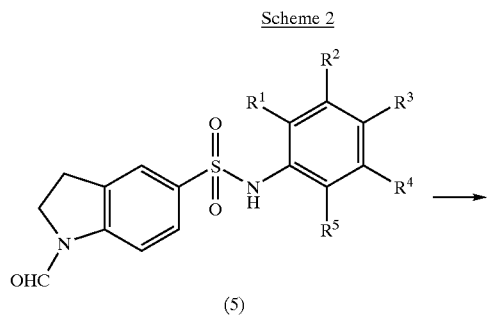

(5)

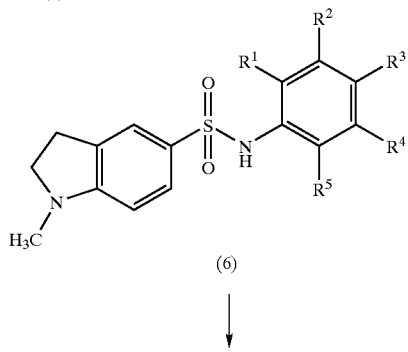

(6)

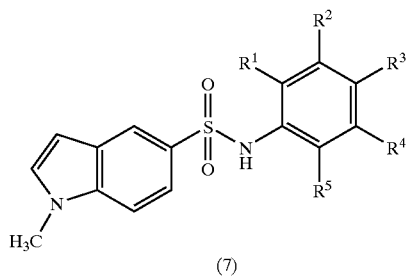

(7)

As shown in Scheme 2, compounds of formula (5) can be converted to compounds of formula (6) by treatment with a reducing agent. Representative reducing agents include borane-methyl sulfide complex, sodium borohydride, a mixture of lithium aluminum hydride and aluminum trichloride, and a mixture of sodium cyanoborohydride with zinc iodide. Examples of solvents used in these reactions include THF, diethyl ether, 1,2-dimethoxyethane, and methyl tert butyl ether. The reaction is conducted at about −5° C. to about 35° C. Reaction times are typically about 1 to about 4 hours.

Conversion of compounds of formula (6) to compounds of formula (7) can be accomplished by treatment with an oxidizing agent. Representative oxidizing agents include palladium on carbon, platinum on carbon, palladium hydroxide on carbon, salcomine and oxygen, barium manganate, and 2,3-dichloro-5,6-dicyano-1,4-benzoquinone (DDQ). Examples of solvents used in these reactions include THF, diethyl ether, 1,2-dimethoxyethane, methanol, and methyl tert butyl ether. The reaction can be conducted at about −5° C. to about 100° C. and depends on the method chosen. Reaction times are typically about 8 to about 24 hours.

Scheme 3

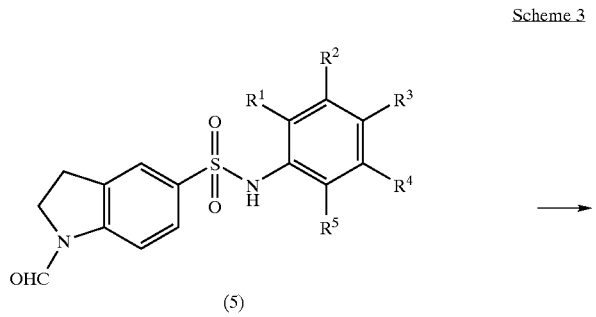

(5)

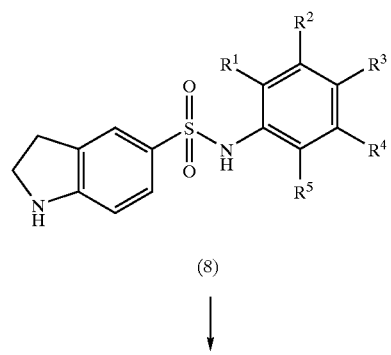

(8)

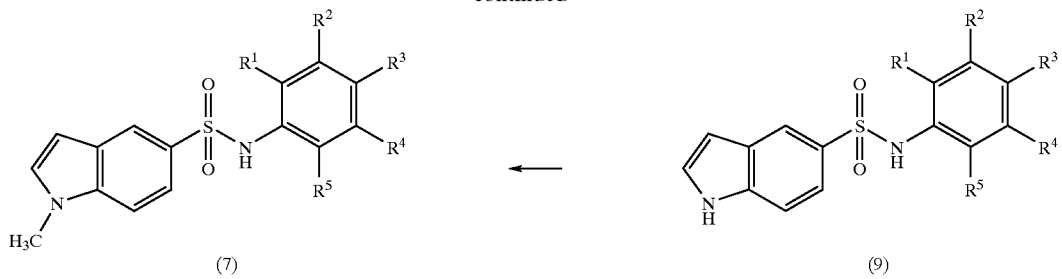

An alternate route to compounds of formula (7) is shown in Scheme 3. Compounds of formula (5) can be converted to compounds of formula (8) by treatment with a deformylating agent. Representative deformylating agents include hydrochloric acid, hydrochloric acid in dioxane, hydrogen peroxide, and sodium hydroxide. Examples of solvents used in these reactions include methanol, ethanol, isopropanol, and butanol. The reaction is conducted at about 20° C. to about 60° C. and depends on the method chosen. Reaction times are typically about 5 minutes to about 24 hours.

Compounds of formula (8) can be converted to compounds of formula (9) using the various oxidative conditions described in Scheme 2.

Conversion of compounds of formula (9) to compounds of formula (7) can be accomplished by treatment with a methylating agent and a base. Representative methylating agents include dimethylsulfate, methyl iodide, and methyl triflate. Examples of bases include sodium hexamethyldisilazide, lithium hexamethyldisilazide, and potassium hexamethyldisilazide. Representative solvents include THF, diethyl ether, methyl tert butyl ether, and 1,2-dimethoxyethane. The reaction is conducted at about 0° C. to about 25° C. and depends on the method chosen. Reaction times are typically about 15 minutes to about 24 hours.

Scheme 4

As shown in Scheme 4, compounds of formula (7) can be converted to compounds of formula (10) by treatment with N,N-dimethylaminoacetyl chloride or N,N-dimethylaminoacetyl chloride hydrochloride in the presence of base. Representative bases include 4-pyrrolidinylpyridine, DMAP, triethylamine, diisopropylethylamine, and mixtures thereof. Typical solvents used in these reactions include dichloromethane, chloroform, THF, and ethyl acetate. The reaction is conducted at about 0° C. to about 30° C. and depends on the solvent chosen. Reaction times are typically about 2 to about 24 hours.

The invention will now be described in connection with other particularly preferred embodiments of Schemes 1–4, which are not intended to limit its scope. On the contrary, the invention covers all alternatives, modifications, and equivalents which are included within the scope of the claims. Thus, the following examples will illustrate an especially preferred practice of the invention, it being understood that the examples are for the purposes of illustration of certain preferred embodiments and are presented to provide what is believed to be the most useful and readily understood description of its procedures and conceptual aspects.

EXAMPLE 1

1-formyl-5-indolinesulfonyl Chloride

A solution of indoline (10 g, 840 mmol) in dichloromethane (400 mL) was treated with 88% formic acid (48.8 g, 924 mmol), heated to reflux, and stirred for 2.5 hours. The mixture was concentrated to 2/3 of the original volume, diluted with 1,2-dichloroethane (200 mL), and again concentrated to 2/3 of the original volume to provide a solution of N-formylindoline in 1,2-dichloroethane, which was used without further purification.

A 17% (w/w) solution of N-formylindoline in 1,2-dichloroethane (100 g, 680 mmol) was cooled to 5° C., treated with chlorosulfonic acid (90.4 mmol, 1.35 mol) at a rate which kept the internal temperature <25° C., heated to 70° C., treated with thionyl chloride (99.2 mL, 1.35 mol), and stirred for 2 hours. The mixture was cooled to 5° C., quenched with water (1.0 L) at a rate which kept the internal temperature <25° C., warmed to 10° C., diluted with heptane (1.0 L), and stirred for 30 minutes. The resulting precipitate was filtered, washed with water (6×1 L) until the filtrate pH was 4.5, washed with heptane, and partially dried under vacuum at 40° C. to provide the desired product (solid assay for 157 g (94%) of 1-formyl-5-indolinesulfonyl chloride. The product was used directly in the next step without further purification.

EXAMPLE 2

1-formyl-N-(3,4,5-trimethoxyphenyl)-5-indolinesulfonamide

A room temperature mixture of Example 1 (153.5 g, 0.625 mol), 3,4,5-trimethoxyaniline (109 g, 0.595 mmol), and sodium bicarbonate (75 g, 0.895 mol) in ethyl acetate (1.1 L)

and water (1.05 L) was stirred for 20 hours, treated with methyl tert-butyl ether (1 L), stirred for 1 hour, filtered, washed with water (2×500 mL) and methyl tert-butyl ether (2×300 mL), and dried under vacuum at 50° C. for 20 hours to provide 223.4 g of the desired product (95.7%) as a mixture of rotamers.

mp 200–201° C.;

$^1$H NMR (300 MHz, DMSO-d$_6$) δ 10.06 & 9.06 & 8.51 (3s, 1H total), 7.99–7.51 (m, 3H), 6.42 (s, 2H), 6.41 (d, 1H), 4.17 & 3.93 (2t, 2H total), 3.68 (s, 6H), 3.57 (s, 3H), 3.13 (m, 2H);

$^{13}$C NMR (75 MHz, DMSO-d$_6$) δ 159.08, 152.98, 145.28, 144.91, 133.96, 133.82, 133.09, 127.35, 127.23, 124.52, 123.79, 114.94, 109.80, 97.51, 60.04, 55.75, 46.91, 44.72, 26.84, 26.22.

EXAMPLE 3

1-methyl-N-(3,45-trimethoxyphenyl)-5-indolinesulfonamide

A 0–3° C. solution of Example 2 (211.7 g, 0.54 mol) and sodium borohydride (30.66 g, 0.81 mol) in THF (1.06 L) was treated dropwise with trifluoroacetic acid (92.45 g, 0.81 mol) while keeping the internal temperature <14° C. The mixture was warmed to room temperature, stirred for 2 hours, and slowly quenched with water (3 L) while keeping the internal temperature <30° C. The mixture was stirred for 1 hour, filtered, washed with water (2×2 L) and methyl tert-butyl ether (1×1 L), and dried under vacuum at 50° C. for 20 hours with a nitrogen purge to provide 190.5 g of the desired product (93.4%).

mp 170–171° C.;

$^1$H NMR (300 MHz, CDCl$_3$) δ 7.54 (dd, 1H), 7.40 (b dd, 1H), 7.18 (s, 1H), 3.77 (s, 3H), 3.73 (s, 6H), 3.46 (t, 2H), 2.94 (t, 2H), 2.80 (s, 3H);

$^{13}$C NMR(75 MHz,CDCl$_3$) δ 156.58, 153.28, 135.01, 133.25, 130.19, 129.24, 124.98, 123.24, 104.31, 98.86, 60.84, 56.02, 54.91, 34.19, 27.63.

EXAMPLE 4

1-methyl-N-(3,4,5-trimethoxyphenyl)-1H-indole-5-sulfonamide

A 0° C. slurry of N-(3,4,5-trimethoxyphenyl)-1-methylindoline-5-sulfonamide (11.3 g, 0.030 mol) in THF (130 mL) was treated with 2,3-dichloro-5,6-dicyano-1,4-benzoquinone (7.15 g, 0.0315 mol), stirred for 4 hours, warmed to 25° C., and stirred for 10 hours. The mixture was concentrated to half of its original volume, diluted with methyl tert-butyl ether (70 mL), cooled to 0° C., stirred for 2 hours, and filtered. The resulting solid was washed with methyl tert-butyl ether (50 mL), dried, and recrystallized from acetonitrile and methyl tert-butyl ether to provide 9.2 g of the desired product (81%).

mp 188–189° C.;

MS (ESI(+)) 377 (M+H)$^+$;

$^1$H NMR (300 MHz, DMSO-d$_6$) δ 10.00 (br s, 1H), 8.14 (m, 1H), 7.63 (m, 2H), 7.55 (d, 1H), 6.68 (d, 1H), 6.48 (s, 2H), 3.86 (s, 3H), 3.69 (s, 6H), 3.58 (s, 3H);

$^{13}$H NMR (75 MHz, DMSO-d$_6$) δ 152.8, 137.8, 134.2, 133.6, 132.2, 129.7, 127.0, 120.7, 119.2, 110.3, 101.9, 97.2, 60.0, 55.7, 32.8.

EXAMPLE 5

N-((dimethylamino)acetyl)-1-methyl-N-(3,4,5-trimethoxyphenyl)-1H-indole-5-sulfonamide A solution of Example 4 (20.0 g, 53.2 mmol) in THF (250 mL) at room temperature was treated with dimethylaminoacetyl chloride hydrochloride (12.3 g, 77.8 mmol), DMAP (650 mg, 5.3 mmol), and diisopropylethylamine (25.2 g, 195.0 mmol), stirred for 8 hours, and concentrated to ⅓ its original volume. The mixture was diluted with ethyl acetate (400 mL), washed with 5% NaHCO$_3$ (2×200 mL) and water (200 mL), dried (Na$_2$SO$_4$), filtered, concentrated to a volume of 120 mL, diluted with methyl tert-butyl ether (120 mL), stirred for 18 hours, cooled to 0° C., stirred for 2 hours, and filtered. The resulting solid was washed with 1:1 ethyl acetate/methyl tert-butyl ether (100 mL) and dried under vacuum to provide 22.5 g (92%) of the desired product.

mp: 200–203° C.;

MS (ESI(+)) m/z 462 (M+H)$^+$;

$^1$H NMR (DMSO-d$_6$): δ 8.36 (d, J=1.8 Hz, 1H), 7.78 (dd, J$_1$=8.7 Hz, J$_2$=1, 8 Hz, 1H), 7.73 (d, J=8.7 Hz, 1H), 7.61 (d, J=3.0 Hz, 1H), 6.76 (d, J=3.0 Hz, 1H), 6.73 (s, 2H), 3.92 (s, 2H), 3.82 (s, 3H), 3.82 (s, 6H), 3.75 (s, 3H), 2.67 (s, 6H);

Anal. calcd. for C$_{22}$H$_{27}$N$_3$O$_6$S.HCl.1.5H$_2$O: C, 50.43; H, 5.77; N, 8.02. Found: C, 50.50; H, 5.93; N, 8.01.

What is claimed is:

1. A process for preparing a compound of formula (5)

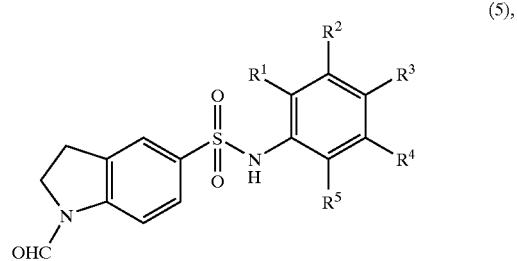

(5), or a therapeutically acceptable salt thereof, wherein

R$^1$ and R$^5$ are independently selected from the group consisting of hydrogen, alkyl, and alkoxy; and R$^2$, R$^3$, and R$^4$ are independently selected from the group consisting of alkyl and alkoxy;

the process comprising:

(a) reacting N-formylindoline with chlorosulfonic acid and thionyl chloride; and (b) reacting the product from step (a) with a base and a compound of formula (4)

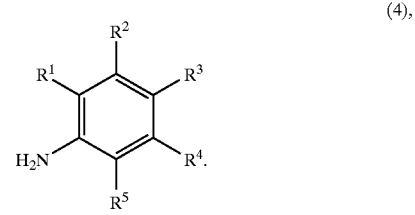

(4),

2. The process of claim 1 wherein the base is a carbonate salt.

3. The process of claim 2 wherein the base is sodium bicarbonate.

4. The process of claim 1 wherein the compound of formula (4) is 3,4,5-trimethoxyaniline.

5. The process of claim 1 which is conducted as a continuous process.

6. The process of claim 1 wherein step (a) is conducted at about 65° C. to about 85° C. for about 1 to about 5 hours.

7. The process of claim 1 wherein the compound of formula (5) is 1-formyl-N-(3,4,5-trimethoxyphenyl)-5-indolinesulfonamide.

8. The process of claim 1 further comprising reacting indoline with an N-formylating reagent to provide the N-formylindoline.

9. The process of claim 8 wherein the N-formylating reagent is selected from the group consisting of 2,2,2-trifluoroethylformate, formic acid, a mixture of formic acid and acetic anhydride, and acetic formic anhydride.

10. The process of claim 9 wherein the N-formylating reagent is formic acid.

11. The process of claim 8 which is conducted as a continuous process.

* * * * *